(12) United States Patent
Ambuel

(10) Patent No.: US 7,087,901 B2
(45) Date of Patent: Aug. 8, 2006

(54) HIGH SPEED ANALYZER USING NEAR INFRARED RADIATION TRANSMITTED THROUGH THICK SAMPLES OF OPTICALLY DENSE MATERIALS

(75) Inventor: Jack Ambuel, Madison, WI (US)

(73) Assignee: Ag Leader Technology, Inc., Ames, IA (US)

( * ) Notice: Subject to any disclaimer, the term of this patent is extended or adjusted under 35 U.S.C. 154(b) by 311 days.

(21) Appl. No.: 10/392,016

(22) Filed: Mar. 19, 2003

(65) Prior Publication Data

US 2004/0021077 A1 Feb. 5, 2004

Related U.S. Application Data

(60) Provisional application No. 60/365,698, filed on Mar. 20, 2002.

(51) Int. Cl.
G01N 21/35 (2006.01)
(52) U.S. Cl. .......................... 250/339.02; 250/339.07; 250/339.01; 356/328
(58) Field of Classification Search ........... 250/339.07, 250/339.01, 339.06, 339.08; 356/329, 328, 356/326, 319, 305
See application file for complete search history.

(56) References Cited

U.S. PATENT DOCUMENTS

| | | | |
|---|---|---|---|
| 4,253,766 A * | 3/1981 | Funk | 356/418 |
| 4,864,356 A | 9/1989 | Asano et al. | |
| 4,868,573 A * | 9/1989 | Wittmer | 341/157 |
| 5,021,662 A * | 6/1991 | Johnson | 250/339.02 |
| 5,303,027 A * | 4/1994 | Kuderer et al. | 356/328 |

(Continued)

Primary Examiner—Albert Gagliardi
(74) Attorney, Agent, or Firm—Daniel A. Rosenberg; Kent A. Herink; Emily E. Harris

(57) ABSTRACT

The present invention relates to an instrument for measuring in relatively short periods of time concentrations of constituents in optically dense materials using the spectra near infrared radiation transmitted through thick samples of the material while the material is either stationary or flowing. The invention uses a broadband incandescent intensity stabilized light source combined with collimating optics to transmit a parallel beam of light through the material under test. The light transmitted through the material is then collected by a focusing lens and imaged onto a rectangular entrance slit of a special purpose spectrometer. This spectrometer has no moving parts and employs a fixed diffraction grating to physically spread the image of the entrance slit into a continuous range of wavelengths. A portion of the diffracted slit images covering the selected portion of the near infrared range is focused onto an array of individual rectangular photodiodes. By using relatively large area photodiodes and a relatively small number of photodiodes, high sensitivity is achieved and low intensity radiation levels can be measured quickly. By using a relatively narrow spectral range, medium resolution can be achieved. The outputs of each photodiode, or the outputs of a selected number of the photodiodes, are fed into current to voltage converters: either resistive (instantaneous) or preferred capacitive (integrating). Thus the outputs of all photodiodes are measured in parallel, which reduces the time to acquire the spectra. The gain of these current to voltage converters is programmable so that both high intensity and low intensity near infrared radiation levels can be measured without reducing the intensity of the radiation incident on the material under test and thereby eliminating the need for moving parts in the spectrometer. After the spectra are acquired, they are operated on by models developed to predict the percentages of various constituents in the material. These models are pre-calibrated using spectra obtained from materials of known concentrations and developed using chemometric, neural net, and/or genetic algorithms.

14 Claims, 6 Drawing Sheets

U.S. PATENT DOCUMENTS

| | | | |
|---|---|---|---|
| 5,422,483 A * | 6/1995 | Ando et al. | 250/339.02 |
| 5,663,559 A * | 9/1997 | Auzerais et al. | 250/269.1 |
| 5,751,421 A | 5/1998 | Wright et al. | |
| 5,933,235 A * | 8/1999 | Sampei et al. | 356/326 |
| 5,991,025 A * | 11/1999 | Wright et al. | 356/328 |
| 6,100,526 A * | 8/2000 | Mayes | 250/339.11 |
| 6,528,791 B1 * | 3/2003 | Williams et al. | 250/339.13 |
| 6,646,264 B1 * | 11/2003 | Modiano et al. | 250/339.07 |
| 6,707,556 B1 * | 3/2004 | Turner et al. | 356/436 |
| 6,851,662 B1 * | 2/2005 | Panigrahi et al. | 356/326 |

* cited by examiner

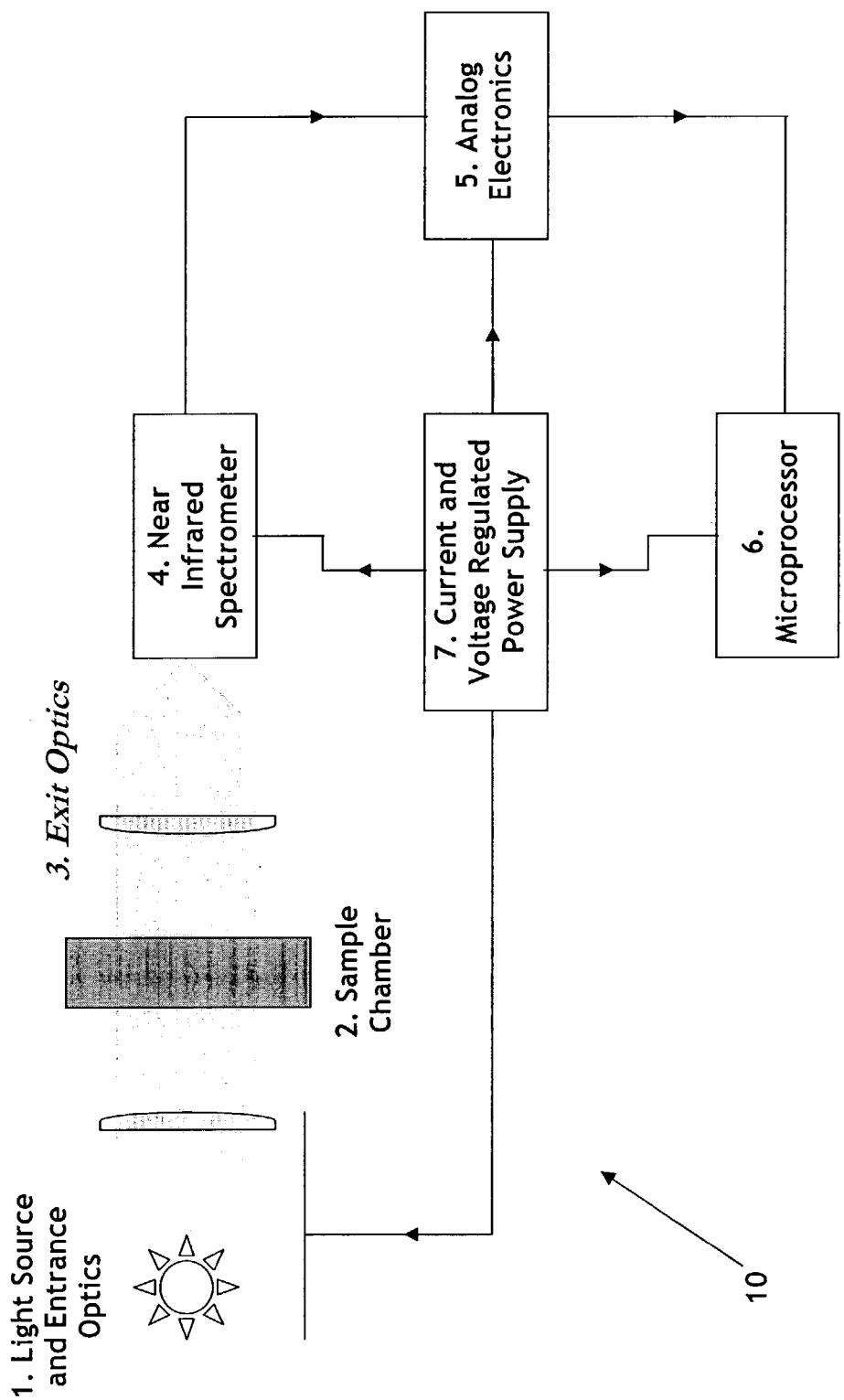
*Figure 1: Near Infrared Transmittance Analyzer for Stationary Material*

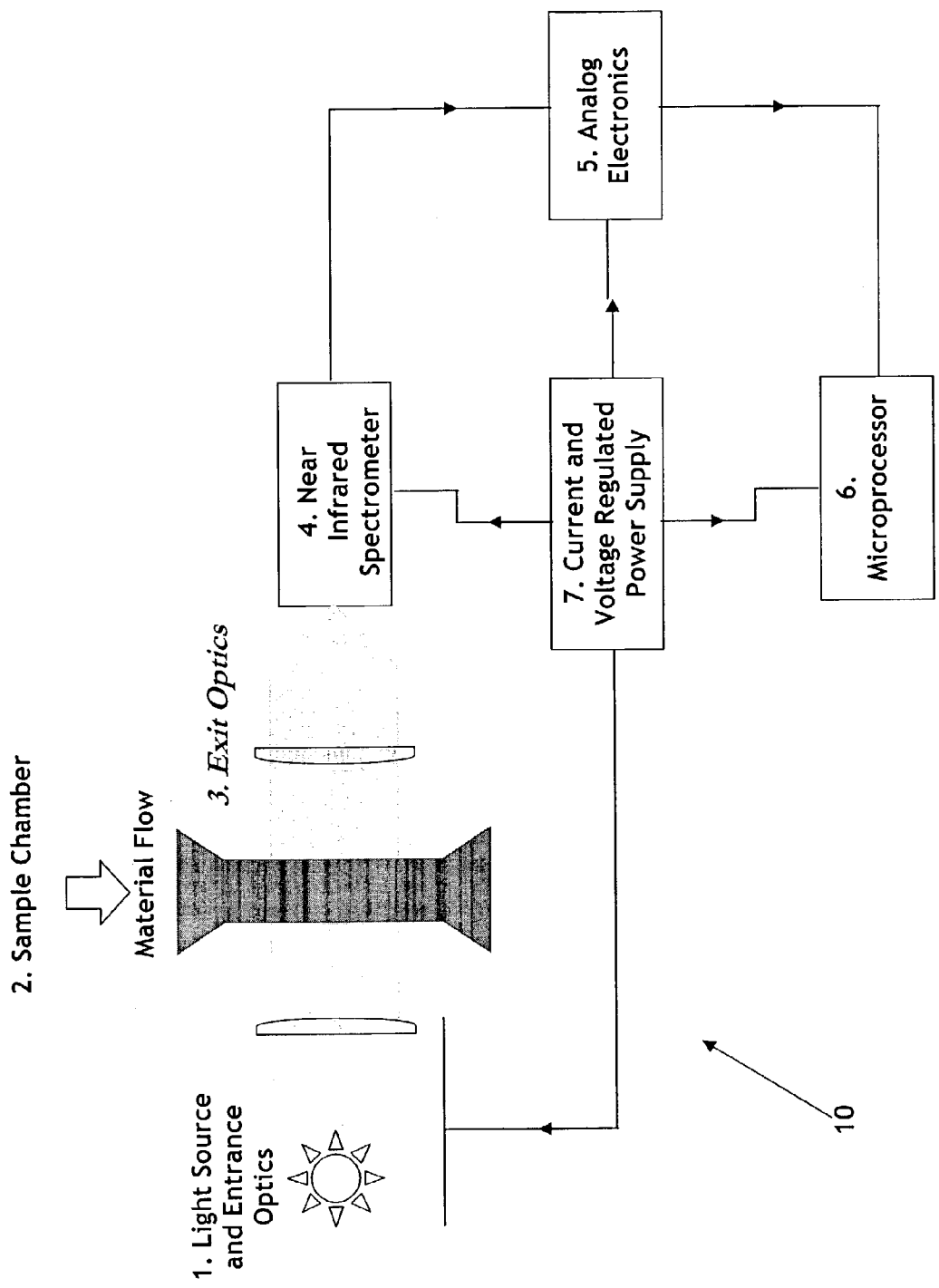
Figure 2: Near Infrared Transmittance Analyzer for Flowing Material

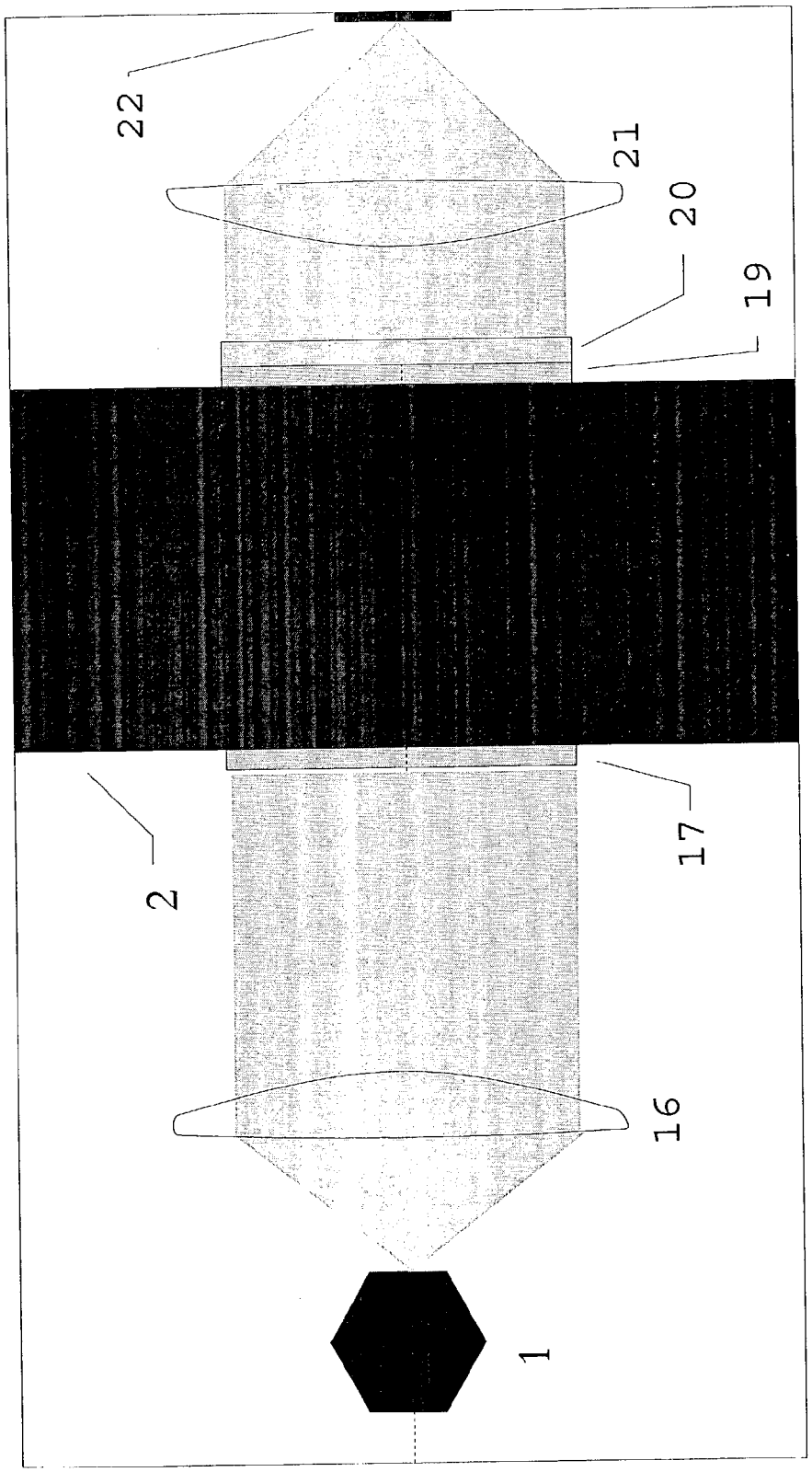
Figure 3: Light Source, Entrance Optics, Sample Chamber, and Exit Optics

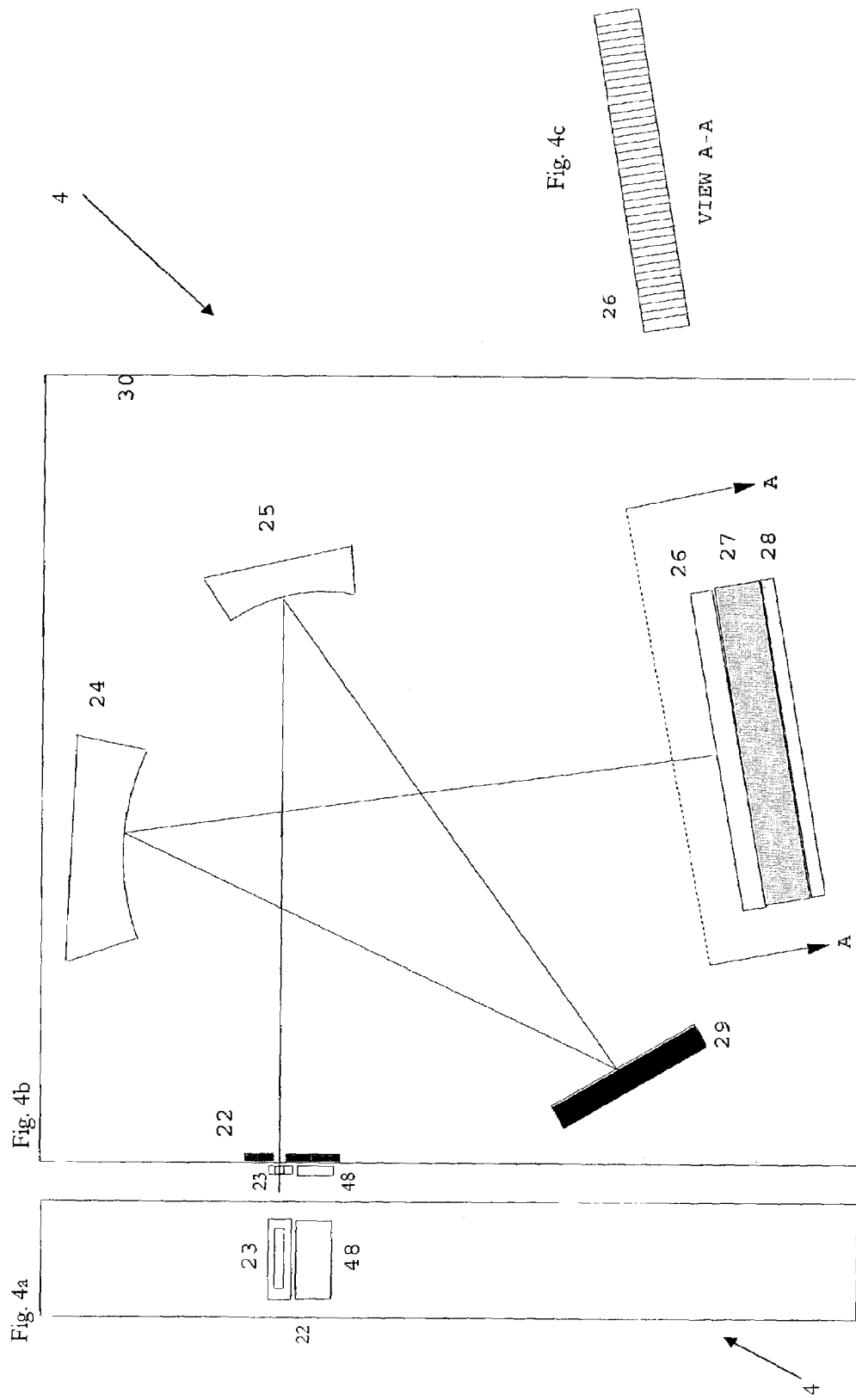
Figure 4 a-c: Spectrometer Block Diagram

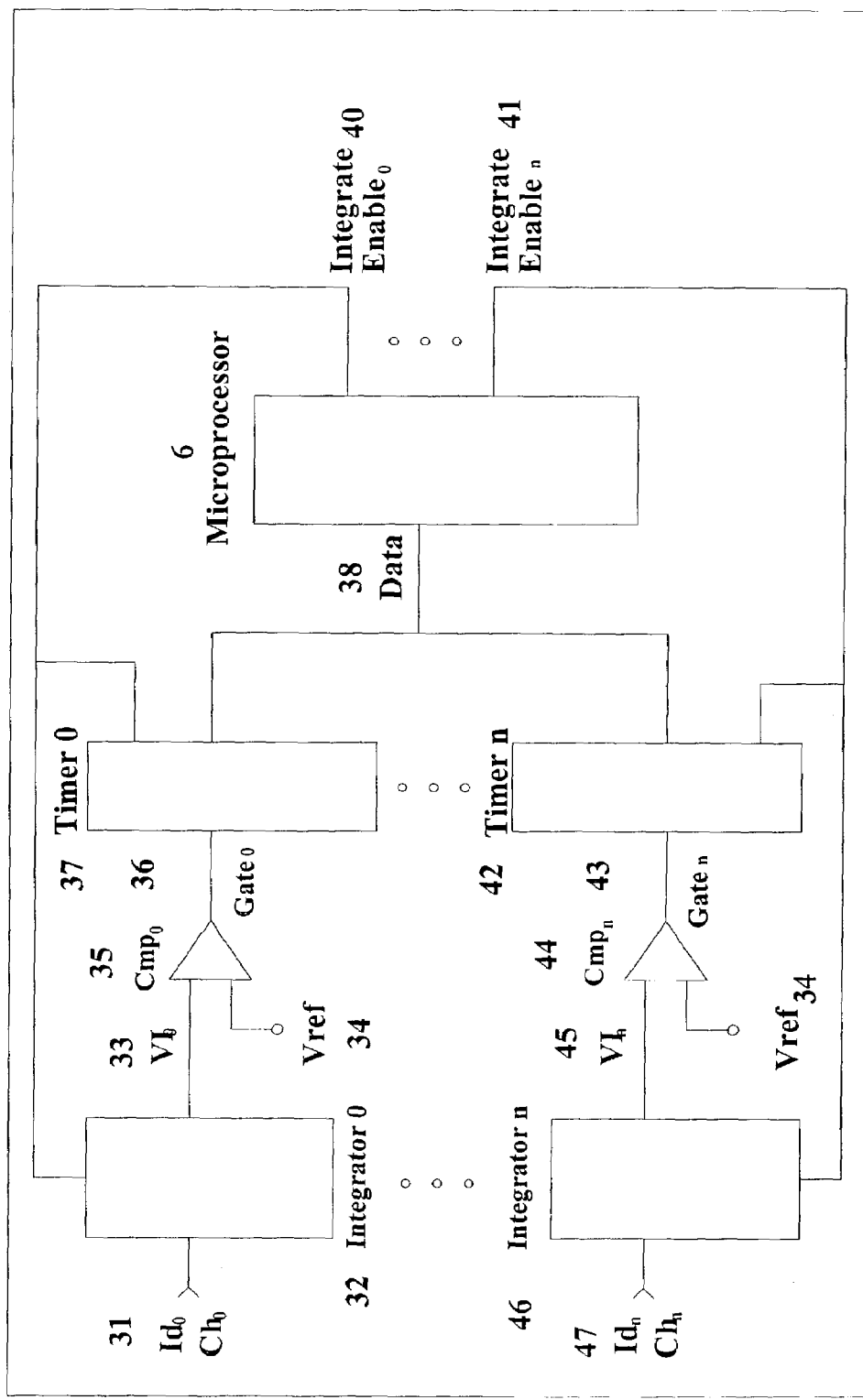
Figure 5: Electronics Block Diagram

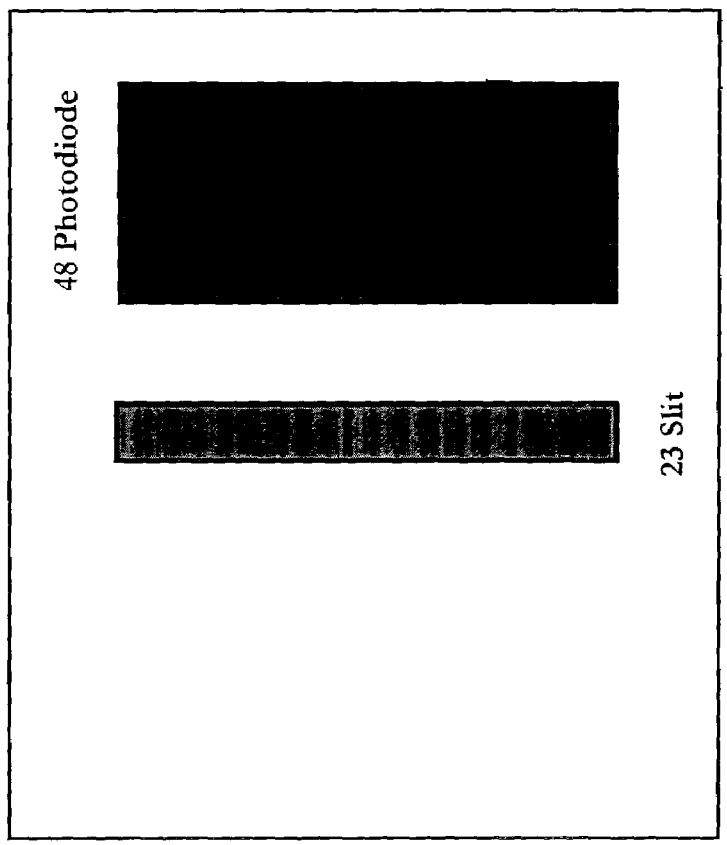
Figure 6: Slit and Off Axis Photodiode Assembly

HIGH SPEED ANALYZER USING NEAR INFRARED RADIATION TRANSMITTED THROUGH THICK SAMPLES OF OPTICALLY DENSE MATERIALS

RELATED APPLICATIONS

The present application claims priority to U.S. Provisional Patent Application No. 60/365,698, filed on Mar. 20, 2002, and incorporates the same by reference thereto.

FIELD OF THE INVENTION

The present invention relates to means for measuring in relatively short periods of time constituents in optically dense materials using medium resolution spectra in the near infrared range transmitted through thick samples of the material while the material is either stationary or flowing. More particularly, though not exclusively, the present invention relates to a method and apparatus using a specific type of near infrared spectrometer developed for this purpose in combination with a spectral based model to measure percentages of the major constituents of stationary or flowing material such as grains, processed foods, pharmaceuticals, chemicals, and other industrial or agricultural products.

BACKGROUND OF THE INVENTION

The measurement of near infrared (NIR) spectra is over 200 years old and research into NIR analyzers began over 50 years ago. "The foundations for modern NIR analysis began to be laid in the 1950's when the USDA had embarked on a programme of research aimed at developing chemico-physical methods for rapidly assessing the quality of agricultural commodities." (Osborne et al., 1993, p 3).

NIR Analyzers have been used for over 30 years to measure constituents of grain, fruit, milk, and meat. After initial applications in the agricultural area, instruments with industrial applications were developed. NIR analyzers for pharmaceuticals, refining, chemical manufacturing, and medical diagnostics emerged.

The function of NIR quantitative analyzers is to predict or estimate the concentrations of various constituents in a substance using the NIR spectra of energy that has passed through at least a portion of that substance. All NIR analyzers perform the same basic operations:

1. Generate energy in some portion of the NIR band (roughly 700 to 2500 nm);
2. Either temporally, spatially, or in combination separate the NIR energy into narrow adjacent bands;
3. Apply energy to the substance under test;
4. Collect a portion of the energy that has passed through part or all of the substance;
5. Measure and record the intensity of the collected energy in one or more of the narrow bands using a suitable detector; and
6. Apply the spectral magnitudes at selected wavelengths as inputs to models developed to predict concentrations of different constituents.

The second, third, and fourth operations are not necessarily performed in the sequence listed. For example, if the energy is spectrally separated in time only or both in time and space, this is typically done before the narrow band energy is applied to the substance. If instead the energy is only separated spatially, this operation is typically performed on the collected portion of the energy that has passed through the substance.

There are a number of different devices or techniques that can be used to accomplish each of the six main operations of an NIR analyzer:

1. NIR Energy Generation:
   Tungsten Halogen Lamp
   Light Emitting Diode (LED)
2. Spectral Separation:
   Scanning or oscillating diffraction grating
   Fixed diffraction grating
   Rotating narrow band filter
   Rotating variable filter
   Fourier Transform (FT) Interferometer
   Acousto-Optical Tunable Filter (AOTF)
3. NIR Energy Delivery to Substance
   Collimating Optics—Direct Output
   Collimating Optics with Intervening Fiber Optics
4. NIR Energy Collection From Substance
   Reflected Energy Focusing Optics—Direct Output
   Reflected Energy Focusing Optics with Intervening Fiber Optics
   Transmitted Energy Focusing Optics—Direct Output
   Transmitted Energy Focusing Optics with Intervening Fiber Optics
5. Measurement of Collected NIR Energy.
   Single Detector
   Detector Array (DA) with Serial Output
   The detector type used depends on the wavelength range of the analyzer. Common detector types are:
   Photomultiplier
   Silicon Photodiode
   InGaAs photodiode
   PbS photoresistor
6. Prediction of Constituent Concentration:
   Chemometric Models: MLR, PLS, PCA
   Neural Net Models
   Genetic Algorithms
   Combinations of these The energy collected can be broadly categorized as belonging to one of two main types: diffuse reflectance spectra and transmitted spectra. For diffuse reflectance analyzers, the delivery optics and the collection optics are placed on the same side of the substance so that the collection optics receives near infrared radiation reflected diffusely off of the substance being measured. For transmittance analyzers, the delivery optics and collection optics are placed on opposite sides of the substance so that the collection optics receives radiation that has been transmitted through the substance being measured.

Commercial NIR analyzers first appeared in the 1970's in the food and agriculture industry (Osborne et al., 1993, pg. 3). The analyzers were designed to measure various constituents of food such as protein, oil, and starch. For the first decade, all commercial instruments were filter based (Osborne et al., 1993, pg. 5). Filter instruments continued to dominate into the middle of the 1980's:

"The two main methods by which most commercial near-infrared instruments generate wavelengths are the discrete filter and the tilting filter principles." (Williams and Norris, 1987, pg. 113)

Although filter instruments dominated for the first 10 to 15 years in commercial instruments there was another wavelength separation technique that found early favor in research analyzers and on which some commercial units were based. That technique was the scanning monochromator (SM) using a motor driven diffraction grating (Williams and Norris, 1987, pg. 126–127; Burns and Ciurczak, 2001, pg. 61–65).

Just as filter based monochromators dominated initial commercial instruments, reflectance spectroscopy was also favored over transmittance. This was mainly due to the fact that the earlier instruments used wavelengths in the 1200 to 2500 nm range (Naes and Isaksson, 1992, pg. 34).

Diffuse reflectance analyzers have several advantages over transmittance analyzers:
1. Many substances being measured are optically dense (opaque). Therefore, for a given resolution spectrometer and given source intensity, use of transmittance spectra instead of reflectance spectra requires use of thinner samples (short optical path lengths), high powered sources, and/or an integrating detector with long integration times; and
2. The mechanical design of reflectance analyzers is sometimes simpler than transmittance spectrometers as both source and detector are placed on the same side of the sample.

There are, however, disadvantages to reflectance analyzers. Some of the major disadvantages are:
1. Reflectance spectrometers only measure a thin layer of the surface of the substance being measured. This is a disadvantage if the material is not homogeneous. In contrast, transmittance spectrometers measure the entire body of material;
2. Reflectance spectrometers require use of a separate reference to establish the reference signal. An ideal reference material will diffusely reflect all incident radiation in the wavelength range of interest. Typically the reference material is inserted mechanically between the incoming radiation and the sample window when a reference reading is made; and
3. Reflectance analyzers are affected more than transmittance analyzers by scattering or dusty environments (Osborne et al., 1993, pg. 92–93). This problem is most severe when granular material such as grain is being measured. When a thin layer of dust accumulates on the surface of the sample chamber input window, most of the incident radiation will reflect off of the layer of dust and little off of the grain inside the sample chamber. The acquired spectrum is therefore mainly that of the dust. For transmittance, the dust will reduce the signal. It will also change the spectral signature of the source incident radiation illuminating the grain. But the accumulated dust will also change the spectral signature of the reference signal, which is acquired when the sample chamber is empty. As long as the spectral signatures of the incident radiation penetrating the dust are closely matched for reference and sample signals, normalization will eliminate the dust spectra. This will enable an accurate representation of the grain absorption spectrum to be calculated. For reflectance mode spectrometers placement of the reference material inside the sample chamber is difficult or expensive to do. It is normally placed outside of the sample chamber and mechanically moved in front of the sample chamber window when a reference signal is to be acquired. In this situation, the dust spectra will not be removed by normalization.

Although filter and scanning grating based analyzers dominated commercial and research applications initially, in recent years other techniques such as Fourier Transform-Near Infrared (FT-NIR) technology in industrial applications and Diode Array based analyzers have emerged. Transmittance analyzers have also been developed in the past 15 years for use in medical, pharmaceutical, and agricultural measurement and control.

In spite of the progress that has been made in the development of NIR analyzers and their many different uses, there are a number of deficiencies that prevent wider application of the technology. New markets await the development of an NIR analyzer with the following features:
1. Low cost;
2. Rugged: operation in presence of dust and vibration;
3. Temperature Stability;
4. Fast Analysis: Take rapid readings even when the intensity of collected energy is low;
5. Operate in transmittance mode analyzing relatively thick samples of optically dense material;
6. High Dynamic Range: Able to measure a wide range (1,000,000:1) of input intensities automatically; and
7. No moving parts.

An analyzer required to meet all of these criteria precludes the use of many of the devices and techniques used in NIR Analyzers listed above:
1. NIR Energy Generation: Tungsten Halogen Lamps are preferred
   LED's in general have insufficient light output and spectral range
2. Spectral Separation: Fixed Diffraction Gratings are preferred
   Scanning gratings, rotating filters, AOTF and FT-NIR are too slow
   Scanning gratings, rotating filters, and FT-NIR have moving parts, and are vibration sensitive
   Filters are not temperature stable and temperature stabilization is expensive FT-NIR and AOTF are expensive.
3. NIR Energy Delivery to Substance: Collimating Optics is preferred
   Fiber Optics reduces the intensity too much.
4. NIR Energy Collection From Substance: Collection of Transmitted Energy through focusing optics is preferred
   Reflected Energy is susceptible to dust and uses moving parts to measure energy reflected off of reference material
   Fiber Optics reduces intensity too much
5. Measurement of Collected NIR Energy. No Suitable Choice
   Single Detector is too slow and requires moving parts. Wavelengths have to be scanned which is too slow, requires moving parts, and is subject to vibration.
   Detector Array (DA) with Serial Output: is too slow as output of array has to be scanned serially. The elements of typical diode arrays are too small so that outputs for low level intensity signals are too low.
   The detector type used: Silicon is preferred
      Photomultipliers are too expensive
      InGaAs photodiode is too expensive, insensitive and requires temperature stabilization
      PbS photoresistor is too expensive, insensitive and requires temperature stabilization There are no commercially available spectrometers that can be used to construct an NIR analyzer with the requirements specified above. The closest devices available are the diode array spectrometers such as the S2000 from Ocean Optics. But these suffer from a number of drawbacks. The diode arrays have a large number of photodiodes—from 512 to 2048. This means that the power incident on each photodiode is very low. On top of that, the arrays are scanned serially (as they must be with so many detectors). Thus low intensity signals that would come from NIR energy transmitted through relatively thick samples of optically dense material would take a long time to acquire if they could be acquired at all. In addition the dynamic range of the instrument is limited and would not permit acquisition of a reference signal that is 1000× greater or more in intensity than the sample signal. A neutral density filter would have to be mechanically inserted when the sample chamber is empty in order to acquire and measure the reference signal. Finally, most of the small medium priced diode array based spectrometers are designed only for fiber optic inputs, decreasing the signal strength even further. In summary, the diode array based spectrometers available today are too slow, have too little dynamic range, and do not collect enough energy to meet the specified requirements.

SUMMARY OF THE INVENTION

The present invention relates to means for measuring in relatively short periods of time constituents in optically dense materials using the spectra of near infrared radiation transmitted through even relatively thick samples of the material while the material is either stationary or flowing. The invention uses a broadband incandescent intensity controlled light source combined with collimating optics to transmit a parallel beam of light through the material under test. The light transmitted through the material is then collected by a focusing lens and imaged onto a rectangular entrance slit of a special purpose spectrometer. This spectrometer has no moving parts and employs a fixed diffraction grating to physically spread the image of the entrance slit into a continuous range of wavelengths. A portion of that diffracted slit image covering a portion of the near infrared range is imaged onto an array of individual rectangular photodiodes. The slit dimensions are the same as the individual photodiode dimensions. The slit and photodiodes are oriented in the same direction with the long side of the slit parallel to the long sides of the individual photodiodes. By using arrays with a relatively small number of large active area photodiodes, high sensitivity is achieved and low intensity radiation levels can be measured quickly. By using a relatively narrow spectral range, medium resolution can be achieved. The outputs of each photodiode, or the outputs of a selected number of the photodiodes are fed into current to voltage converters: either resistive (instantaneous) or the preferred capacitive (integrating). Thus the outputs of all photodiodes are measured in parallel. This parallel operation also reduces the time to acquire the spectra. After the spectra are acquired, they are operated on by models developed to predict the percentages of various constituents in the material. These models are pre-calibrated using spectra obtained from materials of known concentrations and developed using chemometric, neural net, and/or genetic algorithms.

BRIEF DESCRIPTION OF THE DRAWINGS

FIG. 1 is a block diagram of a NIR transmittance analyzer designed to analyze stationary material.

FIG. 2 is a block diagram of the NIR transmittance analyzer designed to analyze flowing material.

FIG. 3 is a diagram of a light source, entrance optics, sample chamber, and exit optics of the analyzer.

FIG. 4a is a front view of a spectrometer of the analyzer.

FIG. 4b is a side view of the spectrometer.

FIG. 4c is a view of a photo diode array of the spectrometer shown from the line A—A of FIG. 4b.

FIG. 5 is a block diagram of an electronics portion of the analyzer.

FIG. 6 is a front view of a slit and off axis photodiode assembly of the spectrometer.

DETAILED DESCRIPTION OF THE INVENTION

The following description of the present invention applies to its preferred embodiment. Those of ordinary skill in the art will understand that the present invention, however, is not limited to the described embodiment.

FIGS. 1–2 show a block diagram of the NIR analyzer 10 for use on stationary and flowable material respectively. Seven major components of the analyzer 10 are identified in FIGS. 1–2. These components and their functions are:

Light source and entrance optics, comprising an incandescent light source 1 that generates a broad spectrum of radiant energy including a continuous component in the selected near infrared range. Part of this radiant energy is collected by a lens and collimated into an approximately parallel beam. This beam is transmitted through a transparent window 17 into the sample chamber 2 holding the material;

Sample chamber 2 is a fixed rectangular chamber for holding the material whose constituents are to be measured, with the transparent entrance window 17 and a transparent exit window 18 attached to opposing sides that are transparent to visible and near infrared radiation;

Exit optics, consisting of a diffuser 20 to further homogenize radiation from different parts of the sample chamber; and a focusing lens 21 to focus the radiation emerging from the diffuser onto an entrance slit/detector assembly 22 of a spectrometer 4;

Spectrometer 4 is a near infrared spectrometer for spreading radiation illuminating an entrance slit 23 in a continuous spectrum, with wavelengths covering a narrow band (nominally 200 nm) in the near infrared range, being imaged onto an array 26 of individual photodiode detectors;

Analog electronics comprising a set of integrator-comparator-timer circuits to integrate the output current from each photodiode into a voltage level and measure the time to reach a fixed reference voltage;

Microprocessor 6 with associated embedded program to control the operation of the spectrometer 4 to acquire the integration times which are inversely proportional to spectral intensity incident on each photodiode (as intensity decreases, integration time increases), and operates on the spectral intensities with a suitable model to predict constituent concentrations in the illuminated material; and Current and voltage regulated power supply to maintain constant intensity output from the light source 1.

All of these components combined constitute the near infrared transmittance constituent analyzer 10 whose general operation is detailed in the remaining 5 Figures and is now described. The basic operation of the analyzer 10 is to acquire magnitudes of selected spectral bands (nominally 5 nm in width) in the selected range (nominally 200 nm) of near infrared radiation transmitted through an optically dense material. These spectra are then used to predict concentrations of one of more of the constituents of the material based on the spectral magnitudes. The prediction is done using pre-calibrated models for each constituent with the inputs to each model being the spectral magnitudes and the output being the predicted concentrations. The sequence of events that lead to this result are: generation of a broadband continuous spectrum light that includes a component in the near infrared range selected; illumination of the material under test with a portion of that light; collection of a portion of that light that is transmitted through the material and focusing it on the entrance slit 23 of the spectrometer 4; spreading of the light inside the spectrometer 4 so that the wavelengths in the selected range are imaged onto a photodiode array 26; conversion of the output of each photodiode to a spectral magnitude; operation on all spectral magnitudes by a constituent prediction model to predict constituent concentration in the material. The details of this process are now presented.

Referring to FIG. 3, the light source 1 consists of an incandescent source whose power input is held constant by a voltage and current controlled power supply 7. An example of a suitable light source is a tungsten halogen lamp, with a precisely positioned element, encased in a quartz envelope. Ideally the element dimensions are the same as the slit and photodiode dimensions. A portion of the output of the lamp is collected by a collimating lens 16 and exits the lens as a beam. The beam is directed perpendicular to a transparent window 17 and passes through the window into the material contained in the sample chamber 18. Some of the light is reflected, some scattered, some absorbed, and some transmitted directly through the material. Some of the transmitted and scattered light passes through the exit window 19 out of the sample chamber. The light emerging from the sample chamber 2 is then further homogenized by the diffuser plate 20. A portion of the light emerging from the diffuser plate 20 is collected by a focusing lens 21 and focused onto the entrance slit/detector assembly 22 of the spectrometer 4.

The entrance slit/detector assembly 22 consists of an optically centered entrance slit 23 of rectangular shape and dimensions equal to the dimensions of the individual rectangular photodiodes that make up the photodiode array 26. The entrance slit dimensions are aligned with the individual photodiode dimensions in the sense that the long side of the slit 23 and the individual photodiodes are parallel and the short sides are parallel with reference to the light beam. The assembly 22 also consists of an off center photodiode detector 48 used to measure the relative total intensity of the incoming radiation and is used in the process of taking reference calibration readings.

The light illuminating the off centered detector 48 results in a current output which is measured by the computer and converted to a digital value. The computer uses the digital value to determine whether the sample chamber 2 is empty and a reference spectrum is being acquired or if the sample chamber 2 is full and a sample spectrum is being acquired. The computer then sets the integrator clock accordingly so that the clock period is short for the reference signal and long for the sample signal (see below).

The light focused on the centered entrance slit 23 enters the spectrometer and is collected by a slit collimating mirror 25. The slit collimating mirror 25 collimates the light passing through the slit 23 and directs the beam toward the diffraction grating 29. The diffraction grating 29 spreads the collimated light into a continuum of wavelengths. This diffraction pattern is then focused into a continuum of slit images by a diffraction pattern focusing mirror 24 onto the photodiode array 26. The spectrometer 4 is designed so that the sequence of slit images of unit magnification is focused onto the array 26—one image per photodiode—and each image covers a different narrow band of wavelengths. If the selected near infrared range is 800 nm to 1000 nm, the slit images would start at 800 nm at one end of the array and end at 1000 nm at the other end of the array.

The photodiode array is mounted on a printed circuit board 27 with an aluminum plate and optional kapton flexible heater 28 attached to the back of the printed circuit board. The flexible heater 28 is used to maintain the photodiode array 26 at a constant and slightly elevated fixed temperature so that the outputs of the diode array 26 will not vary with changes in ambient temperature. The heater strip 28 could be replaced with a thermoelectric cooler instead. A third alternative would be to eliminate the temperature control, add a temperature sensor, and calibrate the analyzer 10 at different temperatures. A fourth alternative would be to use no temperature control or monitoring at all, and only use the analyzer 10 when such control is not required.

The output of each photodiode of the photodiode array 26 is independent so that all outputs can be accessed in parallel. The outputs of each photodiode are connected to the printed circuit board 27 of the analog electronics interface module 5. Referring to FIG. 5, on this printed circuit board, a selected number of the photodiode outputs—$Id_0$ 31 through $Id_N$ 47—are connected to integrators—Integrator 0 32 through Integrator n 46. The integrators are controlled by the integrator enable signals—Integrate $Enable_0$ 40 through Integrate $Enable_N$ 41—from the microprocessor 39. When the integrator enable signals are off, the integrator output voltages—$VI_0$ 33 through $VI_n$ 45—are held at zero volts. When the integrators are enabled, the current coming from the individual photo diodes of the photo diode array 26 charge the integrator charge storage devices (capacitors) and the integrator output voltage magnitudes increase over time at rates proportional to the photodiode currents (which are proportional to the intensity of the radiation incident on the photodiodes—the lower the current the lower the intensity). The integrator output voltages are compared with a reference voltage Vref 34 by comparators $CMP_0$ 35 through $CMP_n$ 44. When the magnitude of an integrator output voltage reaches the reference voltage, the output of the corresponding comparator switches off. The output of each comparator—$Gate_0$ 36 through $Gate_n$ 43—serves as an enable input to a timer—$Timer_0$ 37 through $Timer_N$ 42. The timers are also controlled by the integrate enable signals so that when an integrate enable signal is off, the integrator output voltage is zero, the Gate signal is on, and the timer is disabled. When an integrate enable signal is switched on, the Gate signal remains on, and the timer is enabled. When the timer is enabled, it begins counting and continues counting until the corresponding integrator voltage output signal magnitude reaches the reference voltage level. At this time the gate signal is switched off and the timer stops counting.

The master clock for the timers is set depending on whether the sample chamber 2 is empty or full. The off centered photodiode detector 48 next to the spectrometer entrance slit 23 is used to measure the relative total intensity of the radiation that has been collected after passing through the sample chamber 2. If that intensity level is sufficiently high, then the sample chamber 2 is assumed empty and the reference spectra are acquired. The master clock rate is set high. If the intensity is sufficiently low, then the sample chamber 2 is assumed to be full and sample spectra are acquired. The master clock rate is set low in this case.

The final count value from any timer is a measure of the time required for the corresponding integrator voltage to reach the reference voltage. This count is therefore (for an up-counter) inversely proportional to the magnitude of the photodiode current, which in turn is proportional to the intensity of the incident radiation on the photodiode. The final count is inversely proportional to the intensity of radiation over the narrow spectral band illuminating the photodiode. Thus for a low intensity signal, the photodiode current will be low, the integration time long, and the count high. For a high intensity signal, the photodiode current will be high, the integration time short, and the count low.

The final counts for each timer will be different because the radiant intensities on each photodiode will be different. The final counts will be representative of the spectral absorption signature in the selected near infrared range (800 to 1000 nm, for example) of the radiation transmitted through the material under test. Thus for a low intensity signal, the absorption is high and the count is high. For a high intensity signal, the absorption is low and the count is low. The final counts are read by the microprocessor 6 over a data bus 38 connecting the timers to the microprocessor 6.

After acquisition of the final counts, the microprocessor 6 operates on these counts using constituent prediction models to estimate the concentration of different constituents of the material under test. These models are pre-calibrated using materials of known concentrations and developed using chemometric, neural net, and/or genetic algorithms.

The analyzer 10 is designed in order to provide a low cost medium resolution near infrared transmittance instrument with no moving parts capable of measuring at least relatively thick samples of optically dense material quickly, while also capable of measuring high intensity reference signals without changing the intensity of the light incident on the sample chamber. Low cost and ability to measure low signal levels are aided by using standard quartz tungsten halogen lamps and individually addressable large area silicon photodiodes. High speed is accomplished by using individually addressable photodiodes whose outputs are converted in parallel to voltage levels by high gain integrators. Ability to measure a wide range of spectral intensities without changing incident intensity is accomplished by using counters with programmable clock rates. A low clock frequency is used to measure the spectral signature of light transmitted through the sample, and a high clock frequency for the spectral signature of light transmitted through an empty sample chamber (reference spectra). This design also eliminates the need for moving parts. Medium resolution is achieved by restricting the detected range to a nominal 200 nm and by the spectrometer physical design.

In order to design an analyzer that meets the listed specifications, a new spectrometer must be designed. The design must balance cost, source power, energy collection efficiency, resolution, and speed in order to achieve the desired performance. For this spectrometer the first four operations of the NIR analyzer listed in the Background of the Invention would use the preferred devices already identified. The fifth operation—detection—would require use of a device not commonly used in NIR spectrometers: a linear silicon photodiode array 26 with parallel outputs and a small number of large area individual photodiodes. This would be combined with special interface electronics to enable fast stable conversion of the individual detector output photocurrents. The complete spectrometer 4 in its preferred embodiment consists of:

NIR energy generation consisting of a tungsten halogen lamp 1 with electronic stabilization to maintain constant intensity output and lamp element dimensions selected to match as close as possible the spectrometer input slit dimensions;

Spectral separation comprised of a fixed diffraction grating 29 designed to spread the collected energy over the diode array 26 in the preferred wavelength range (800 to 1000 nm, for example);

NIR energy delivery to substance comprising collimating optics is preferred with direct transfer to the sample chamber 2 and through the sample chamber window 17;

NIR energy collection from substance comprising collection of transmitted energy through focusing optics, with direct transfer to the input slit 23 of the spectrometer 4. The lamp filament, collimating optics, and focusing optics are designed so that an image of the filament is focused onto the spectrometer entrance slit 4;

Measurement of collected NIR energy through use of a linear silicon photodiode array 26 of a limited number (less than 50) of relatively large area photodiodes. The photodiodes in the array 26 are individually addressable. Timer based integrators are used to measure the relative intensity of the narrow band radiation incident on each photodiode.

This analyzer 10 involves 5 major changes to typical commercially available diode array spectrometers. One of the most innovative aspects of the design is the use of a diode array comprised of a relatively small number of large area photodiodes (less than 50). Most commercial diode array spectrometers use arrays with 512, 1024, or 2048 detectors. A second related innovation is use of a diode array with individually addressable photodiodes instead of a serial output array. The two innovations combined enable fast conversion of low intensity signals.

The third major innovation in the design is the use of per channel time based integrators with special design features to enable conversion of both low and high level signals while meeting the requirements of fast conversion time, high resolution, and no moving parts. The integrators measure the photocurrents from each photodiode, which are proportional to the intensities of the NIR radiation in each narrow band of wavelengths incident on the individual photodiodes. The timed-based integrators consist of a switched integrator, integrating capacitor, timer, clock, voltage reference, and comparator. With the integrator switched off the capacitor voltage is fixed at 0 volts. When the integrator is turned on, the timer is started and the photocurrent from the associated photodiode begins charging the integrator capacitor. When the capacitor voltage reaches the voltage reference the comparator changes state. This stops the integrator and the timer. The final count in the timer is a measure of the time required to charge the integrator capacitor to the reference voltage level and is inversely proportional to the photodiode current (low current, high count).

The task of meeting the requirements of fast conversion, high resolution, and no moving parts while measuring both high and low level signals is made much simpler if one or more of the timed integrator circuit parameters is made programmable in real time. There are three main parameters that could be made selectable: the integrator capacitor; the timer clock frequency; and the comparator reference voltage. Of these three, it is not practical to switch the capacitor in real time. This leaves just two options: the clock and the reference voltage. The value of the capacitor is preferably fixed.

The value at which the capacitor is fixed depends on which of the three requirements has highest priority. In most applications, fast conversion time will be most important. Therefore, in order to convert low level photocurrents quickly, the lowest practical capacitor value is selected.

The lowest practical value of the integrator capacitor is determined by manufacturing constraints (obtainable accuracy for low valued capacitors), and physical constraints (lowest practical level of stray capacitance). It also depends indirectly on the intensity level of the reference spectrum, the maximum value of the voltage reference, and the maximum clock frequency that is practical. With the integrator capacitance set to a low value, the high photocurrent that occurs when measuring the reference signal will quickly charge the capacitor. If the clock and/or voltage reference levels are too low, then the final count will also be low. If the final count is too low, then the reference signal measuring resolution will be too low. Therefore, both the clock and the voltage reference level are set to their maximum values to enable sufficient resolution. The minimum capacitance value is then equal to the value that will guarantee the minimum acceptable measurement resolution (unless manufacturing or physical constraints require a higher value).

Setting the integrating capacitor, clock rate, and voltage references in this way guarantees satisfactory operation when reference signal measurements are made, but compromises performance and may create problems when measuring low level sample signals. The performance is compromised because the reference voltage level is set to its maximum value. The purpose of this is to slow down the time for the reference signal current to charge the capacitor so that the final count will be high enough to insure adequate measurement resolution. This also slows down the time required for the low level sample spectrum to be acquired increasing the spectral acquisition time and thereby degrading performance. There are other potential problems caused by using the maximum clock frequency and maximum reference voltage. The maximum reference voltage increases the acquisition time as already noted. This coupled with a high clock frequency can result in a large final count if the sample signal intensity is orders of magnitude lower than the reference signal intensity. This problem can be overcome if sufficiently wide counters are used (24 bit or 32 bit instead of 16 bit for example). However there may be practical or cost constraints on the maximum width of the counter.

These two problems are resolved in this design by making both the voltage reference level and the clock frequency programmable. The voltage reference level is set high when measuring high intensity reference signals and low when measuring low intensity sample signals. This enables high resolution measurements for both signals and minimizes conversion time for sample signals. Similarly, the clock frequency is set high when measuring reference signals to enable adequate measurement resolution. The frequency is set low for sample signals in order to minimize the required counter width.

Determination of when reference signals and when sample signals are being measured is accomplished as follows. A separate photodiode 48 external to the spectrometer 4 is mounted near the entrance slit 23 and measures the total intensity of the incoming radiation. This measurement is used to determine whether the sample chamber is full or empty and therefore whether a sample spectrum or reference spectrum is being acquired. The master clock frequency and voltage reference level are then set accordingly.

In summary, the third major innovation consists of using a timed based integrator with programmable clock and voltage reference levels. This circuit enables fast high resolution conversion of both high and low level signals, without the use of moving parts.

The last two modifications—elimination of input and output fiber optics—are necessary to insure adequate sensitivity to low intensity signals. Thus a tungsten halogen lamp is used along with direct throughput collimating and focusing optics to keep the intensity levels received high even after passing through optically dense materials. The last two features are not common to commercially available diode array based spectrometers which use intervening fiber optics, but are found in other commercial analyzers. However, the first three features—large area, individually addressable diode array 26 with variable time base integrators—are unique to this design.

The use of a diode array 26 with a relatively small number of individually addressable large area photodiodes is counter-intuitive because it is generally thought that for a spectrometer, more resolution is better. When discussing diode arrays, it is generally assumed that there will be a large number of photodiodes on the array (Osborne et al., 1993, pg. 120). Spectrometer manufacturers typically provide instruments with many individual photodetectors to maximize the resolution, subject to cost constraints. As technology advances, costs are reduced, and resolution increases. This makes use of these spectrometers in transmittance analyzers more problematic by exacerbating the problems transmittance analyzers have working with optically dense materials.

For wavelength regions where the absorption bands are narrow this belief in the superiority of high resolution instruments is well founded. However, for wavelength regions where constituents have broader absorption bands, the high resolution may not be beneficial or necessary (Osborne et al., 1993, pg. 120; Hildrum et al., 1992, pg. 115). The present invention was designed to take advantage of this and create a transmittance analyzer to rapidly measure constituents with broad absorption bands in optically dense materials. The present invention constitutes a transmittance analyzer that can operate through thick samples of optically dense material and generate results in a short time.

As proof of concept of this invention, a bench top prototype was constructed using commercially available parts where available. This was possible for all components with the exception of the spectrometer which requires a custom design. In place of the spectrometer, six discrete filtered photodiodes were used in a planar array. The filtered detectors used are manufactured by Intor. Each filtered detector consists of a 2 mm×2 mm photodiode chip mounted on the base of a TO-18 package. A bandpass filter is placed in between the photodiode and the TO-18 package window. Six different center wavelengths were selected: 870 nm, 900 nm, 910 nm, 920 nm, 980 nm, and 990 nm. The Full Width Half Maximum of each filter (=width of the pass band at the half power points) was 10 nm. The transmission percentage of all filters was 50% with the exception of the 870 nm filter which had 45% transmission. The parts list for the main components of the prototype and corresponding drawing numbers is given in Table 1:

TABLE 1

Prototype Parts List

| Drawing Number | Part Description: Supplier; Supplier Part Number, and Part Specifications | Notes |
| --- | --- | --- |
| 15 | Light Source: Gilway Technical Lamp L9389 Precision Quartz Tungsten Halogen 50 Watt Lamp | |
| — | Fiber Bundle: Romac FO-BB1/4X6S Six Foot 0.25 inch diameter fiber optic bundle | This part is not shown in the drawings and is not a part of the preferred embodiment or any alternative embodiments. It is |

TABLE 1-continued

Prototype Parts List

| Drawing Number | Part Description: Supplier; Supplier Part Number, and Part Specifications | Notes |
|---|---|---|
| | | included because the prototype constructed for proof of concept was developed by modifying a test fixture used to investigate various off the shelf spectrometers. |
| 16 | Aspheric Condenser Lens: Edmund Scientific J43-991: 57 mm diameter 42 mm EEL Collimating Lens | |
| 17, 18, 19 | Rectangular Grain Sample Chamber with 1/8$^{th}$ inch thick, 2.5 inch × 2.75 inch rectangular Plexiglass input and output windows. Thickness of sample chamber = 1 inch | This sample chamber was custom built. Windows made of glass or sapphire would also be suitable. |
| 20 | Diffuser: Edmund Scientific K45-655 Ground Glass 50 mm × 50 mm Diffuser | |
| 21 | Not Used | |
| 26 | Planar Six Element Filtered Photodetector Array: Intor T18-A870.0/10/45, T18-A900.0/10/50, T18-A910.0/10/50, T18-A920.0/10/50, T18-A980.0/10/50, T18-A990.0/10/50. Bandpass filtered photodiodes with 10 nm FWHM, 45% or 50% transmission, and 2 mm × 2 mm photodiode active area | This filtered photodetector array was custom constructed and used in place of the custom diffraction grating spectrometer |
| 32 | Integrator: Texas Instruments (Burr Brown) ACF2101 | |
| 35 | Comparator: National Semiconductor LM339 | |
| 37 | Timer: Intel 8254 | |

After construction of this prototype, the photodiode currents from the six photodiodes were measured with the grain sample chamber empty and with the sample chamber filled with whole grain wheat (one inch thick). The maximum and minimum photodiode currents for the empty and grain filled chamber were:

Iemptymax=600 na

Iemptymin=170 na

Ifilledmax=30 pa

Ifilledmin=10 pa

Based on design goals of minimum conversion time and maximum resolution, the voltage reference and clock frequencies for both the empty chamber and filled chamber can be determined from these values. The values are determined by applying the Integrator equation that relates the photodiode current, the Integrator output voltage, and the integration time. Assuming the Integrator output voltage is initially zero, the Integrator equation is:

$$T = \frac{CV}{I_{pd}} \text{ where} \qquad \text{Equation 1}$$

$T$ = Integration Time $C$ = Integrator Capacitance $V$ = Integrator Output Voltage $I_{pd}$ = Photodiode current = Integrator current When the Integrator output voltage reaches the comparator reference voltage, the Integrator is stopped. Let the reference voltage be denoted by Vref and the time for the Integrator output voltage to equal the reference voltage be denoted by Tref. Substituting into the Integrator equation gives:

$$T_{ref} = \frac{CV_{ref}}{I_{pd}} \qquad \text{Equation 2}$$

Because the Timer is started when the Integrator is started and stopped when the Integrator is stopped, the relationship between the Timer count and the Integration Time (Tref) is:

$$T_{ref} = NT_C = \frac{N}{f_c} \text{ where } \quad N = \text{Final Count} \qquad \text{Equation 3}$$
$$T_c = \text{Counter Period}$$
$$f_c = \text{Counter Frequency}$$

These equations, combined with the measured photodiode currents can be used to determine how close the prototype system comes to the design goals discussed above. The first step is to determine the capacitance, reference voltage, and clock period when the grain sample chamber is filled with grain. The goal in this case is to minimize the time to read the low level photodiode currents. This can be done by selecting a capacitance value and reference voltage that are as low as practical. A reasonable value for the Integrator capacitor is 25 pico farads. The effects of leakage currents should be relatively easy to control with a capacitor value of this magnitude. Because changing the value of the capacitance is not practical in realtime, this will also be the value used for the empty chamber reading. The reference voltage should also be as low as possible to minimize conversion time. For the prototype a reference voltage setting of 0.325 volts was selected somewhat arbitrarily. With a value this low, it may be necessary to automatically adjust for or measure comparator offset voltages. This automatic adjustment is not difficult to accomplish and so the selected reference level is reasonable.

Substituting the filled chamber photodiode currents, C=25 pf and Vref=0.325 volts into Equation 2 above gives the maximum and minimum conversion times for a grain filled sample chamber:

$$T_{ref\max} = \frac{(25 \times 10^{-12})(0.325)}{(10 \times 10^{-12})} = 0.8125 \text{ seconds} \qquad \text{Equation 4}$$

$$T_{ref\min} = \frac{(25 \times 10^{-12})(0.325)}{(30 \times 10^{-12})} = 0.27083 \text{ seconds}$$

The maximum conversion time is less than one second, which can be considered high speed conversion of the low level transmitted light emerging from the optically dense wheat.

The next step is to determine the counter frequency. Setting the counter period for filled chamber readings is somewhat arbitrary. In general setting a frequency that will provide leeway to cover currents both higher than the expected maximum and lower than the expected minimum is a good practice. The margin provided depends on the application. Given that the Intel 8254 is a 16 bit counter (maximum count=65536), let the count corresponding to the minimum photodiode current be=32500. Substituting this count into Equation 3 and solving for the counter period Tc:

$$T_c = \frac{T_{ref}}{N} = \frac{.8125}{32500} = 25 \ \mu sec \ and \ f_c = 40 \ kHz \qquad \text{Equation 5}$$

Using this value for the clock period, the end count for the maximum photodiode current can be determined again using Equation 3:

$$N_{min} = \frac{T_{ref}}{T_c} = \frac{.27083}{.000025} = 10833 \qquad \text{Equation 6}$$

Having set the reference voltage and clock period for the filled sample chamber, the next step is to set these values for the empty sample chamber. Here there are two design goals—do not overflow the counter and maintain sufficient resolution. In the previous exercise, the value of the capacitor was set to 25 pf and it was noted that the Intel 8254 is a 16 bit counter. Increasing the reference value as high as possible will extend the integration time (thereby guarding against overflow) and help maintain the required resolution. A reference value of 10 Volts is within the operating range of the Integrator and not to close to the maximum voltage output of the integrator. Combining these values with the maximum and minimum empty sample chamber photodiode currents gives:

$$T_{ref\,max} = \frac{(25 \times 10^{-12})(10)}{(170 \times 10^{-9})} = 1.4706 \ milliseconds \qquad \text{Equation 7}$$

$$T_{ref\,min} = \frac{(25 \times 10^{-12})(10)}{(600 \times 10^{-9})} = 0.4167 \ milliseconds$$

To meet the design goal of adequate resolution, the counter clock frequency must be high (period short). The 8264 can run at 2.5 MHz. Selecting a clock frequency of 2 MHz (Tc=500 ns) and substituting into Equation 3 gives:

$$N_{max} = \frac{T_{ref\,max}}{T_c} = \frac{.0014706}{.0000005} = 2941 \qquad \text{Equation 8}$$

$$N_{min} = \frac{T_{ref\,min}}{T_c} = \frac{.0004167}{.0000005} = 833$$

In summary, with a fixed Integrator capacitor value of 25 picofarads, the voltage reference and clock frequency settings for empty and filled sample chambers that enable the prototype to operate as a high speed NIR transmission mode analyzer of optically dense material are:

$T_{cFilled}=25 \ \mu sec$ and $f_{cFilled}=40 \ kHz$ $V_{refFilled}=0.325$ Volts $T_{cEmpty}=500 \ nsec$ and $f_{cEmpty}=2 \ MHz$ $V_{refEmpty}=10.0$ Volts  Equation 9

With these settings, the maximum conversion time is under one second and the high output photodiode currents that occur when the sample chamber is empty can be digitized with sufficient resolution.

While the prototype provides proof of concept, it must still be shown that the preferred embodiment described above will exhibit similar performance. The difference between the prototype and preferred embodiment is the replacement of the diffraction grating based spectrometer with a planar array of individual filtered photodiodes. To demonstrate that the diffraction grating based spectrometer can provide similar performance to the prototype using planar filtered detectors, it suffices to show that the power incident on an individual photodiode element in the photodiode array is comparable in magnitude to the power incident on the corresponding photodiode in the planar filtered detector array. But first, a review of the spectrometer operation will be done.

The diffraction grating based spectrometer 4 consists of an entrance slit 23, two lir rots 24, 25, a diffraction grating 29, and a photodiode array 26. A suitable photodiode array 26 for use in this spectrometer is the UDT Sensors A5V-38, which consists of an array of 38 individual 4.39 mm×0.89 mm photodiodes. With the slit dimensions set equal to the individual photodiode element dimensions (4.39 mm×0.89 mm), the mirrors 24, 25 and diffraction grating 29 are configured so that they create 1:1 images of the illuminated entrance slit 23 on each of the individual photodiode elements. Each slit image has a different center wavelength and the bandwidth of each slit image is approximately 5.25 nm. The center wavelength of the first slit image begins at 802.125 nm at one end of the photodiode array and ends at 997.335 at last slit image. In essence a rainbow of slit images in the near infrared occurs across the face of the photodiode array 26.

In order to compare the two systems, the amount of NIR energy collected by a single filtered detector photodiode is compared with the amount collected by the corresponding photodiode element in the spectrometer photodiode artay 26. For the purposes of this exercise, the NIR intensity incident on all filtered detectors can be approximated as uniform. Similatly, it can be approximated that the intensity across the photodiode array 26 in the diffraction grating based spectrometer 4 is also uniform. The active area of the filtered detector array photodiode is 4 mm$^2$ and the active area of the individual photodiode elements of the photodiode array is 3.9 mm$^2$. In addition, the photodiodes in the array 26 and filtered detectors have essentially the same photosensitivity (approximately 0.6 A/W). Because the active areas and photo sensitivities of the photodiodes are approximately the same for both systems, all that is required to compare the performance of the two systems is to compare the relative NIR intensities (Watts/cm$^2$) incident on the photodiode elements. To do this one must compare the optical throughput of each system.

As an initial approximation, assume that the focusing lens 21 is not present in the diffraction grating based spectrometer analyzer and that the fiber bundle between light source and collimating lens present in the prototype is also present in diffraction grating based spectrometer analyzer 10. With these assumptions, the only difference between the analyzer 10 and the prototype system is that the planar array of filtered detectors is replaced by the diffraction grating based spectrometer 4. Under these conditions, the transmitted NIR intensity incident on the entrance slit 23 to the spectrometer 4 will be equal to the transmitted intensity incident on anyone of the filtered detectors. The throughput of the filtered detectors is approximately 50% (i.e. 50% of the incident NIR is transmitted through the filter to the photodiode). The throughput of the spectrometer for NIR incident on the entrance slit is given by:

$T = S_{AR} E_M R^2$ where $S_{AR}$=Slit Aperture Ratio=Ratio of Slit Area to Photodiode Area $E_M$=Diffraction Grating Efficiency R=Mirror reflection efficiency    Equation 10

By design, the slit dimensions are set equal to the individual photodiode element dimensions (4.39 mm×0.89 mm) and so the slit aperture ratio is 1. Typical diffraction grating efficiency is 0.65 and mirror reflection efficiency is 0.9. Substituting these values into the throughput equation gives T=0.5265. In effect, the throughput for both systems is approximately the same. There is however, one additional factor that must be considered. The bandwidth of the NIR incident on the photodiodes of the filtered detectors is 10 nm, while the bandwidth of the NIR incident on the individual photodiodes of the photodiode array 26 is approximately 5 nm. This reduced bandwidth will cut the incident intensity in half, and therefore cut the photodiode output current in half for a given transmitted intensity. The net result is that the prototype system using filtered detectors would be approximately twice as fast as the diffraction grating based spectrometer analyzer 10.

The slower response time is actually recovered in the preferred embodiment which does not include the fiber optic bundle that couples the light source to collimating lens in the prototype. The light loss in this bundle is approximately 60%. Because the bundle is not present in the diffraction grating based spectrometer analyzer 10, the intensity of NIR transmitted through the grain is more than doubled and the response time will therefore be approximately equal to the prototype system (i.e. conversion times of less than one second). In either case, with or without the fiber optic bundle, the preferred embodiment has been shown to meet all performance claims.

In addition to demonstrating the viability of the preferred embodiment of this invention, the prototype serves as the basis of a modification to the preferred embodiment that may have advantages in certain situations. This modification involves replacing the diffraction grating based spectrometer 4 with a linear variable filter (LVF) and photodiode array spectrometer. This spectrometer is constructed by attaching a linear variable bandpass filter of rectangular shape and covering the 800 nm to 1000 nm range to the face of the UDT A5V-38 photodiode array 26. The mirrors 24, 25, diffraction grating 29, spectrometer housing, and slit 23 would be removed and replaced with the LVF-Photodiode array unit. The LVF-Photodiode array would be placed directly in the path of the transmitted NIR. In principle, the design is functionally equivalent to the prototype design. The only difference is that the individual filtered detectors mounted on some metal plate are replaced with a single package consisting of an integrated array of photodiodes overlaid by a single bandpass filter whose center wavelength varies linearly from one end to the other. The performance of this alternative embodiment would be essentially the same as the preferred embodiment. The conversion times would be similar. While the main objection to using filters still holds—variations due to temperature—these variations are more easily controlled with an LVF. This alternative could become the preferred embodiment if the temperature controlled LVF were to prove more cost effective than the diffraction grating based spectrometer 4.

The foregoing description of the preferred embodiments of the present invention has been presented to illustrate a practical realization of the subject invention. It is not intended to be exhaustive or to limit the invention to the precise form disclosed. Other embodiments are possible without departing from the scope of the invention.

The invention claimed is:

1. A near infrared radiation analyzer for use in analysis of the constituent components of either stationary or flowing relatively optically dense material, said analyzer comprising:
    a light source adapted to produce a beam of light in at least a near infrared spectrum;
    a sample chamber for holding the relatively optically dense material to be analyzed and with an entrance and exit window transparent to said near infrared spectrum and for transmittance of said beam of light;
    a near infrared spectrometer comprising an entrance slit through which said beam of light enters after passing through said exit window of said sample chamber, a slit collimating mirror to collect said light from said slit and reflect it into a nearly parallel beam, a diffraction grating for dividing said beam of light into a plurality of bands of near infrared wavelengths, a diffraction grating focusing mirror to form a continuous row of slit images from said diffracted light with successive images being formed by adjacent narrow bands of near infrared light, a photodiode array comprised of 50 or less individual photodiodes covering said near infrared spectrum said photodiodes individually sensitive to a plurality of bands of near infrared wavelengths, wherein said individual photodiodes generate a current proportional to an intensity of near infrared light detected by said individual photodiodes; and
    electronic circuitry comprised of integrator, comparison, and timer circuits for converting said currents from said individual photodiodes to voltages, comparing those voltages with a reference voltage, and counting the time for said voltages to reach the reference voltage level, and a microprocessor for controlling said circuits and receiving circuit output and for applying algorithms to said output to analyze the material in said sample chamber; and
    a power source for powering said analyzer.

2. The invention in accordance with claim 1 further comprising an off axis photo detector for measuring the overall intensity of said beam of light from said light source after the beam has passed through said sample chamber, and wherein the magnitude of the intensity of said beam of light is used to determine the presence of the material in said sample chamber.

3. The invention in accordance with claim 2 wherein said reference voltage is adjustable in response to said output of said off axis photo detector to allow said electronic circuitry to automatically process a reference signal and a sample signal.

4. The invention in accordance with claim 2 further comprising a programmable master clock wherein the rate of said clock is adjustable in response to said output of said off axis photo detector to allow said electronic circuitry to automatically process a reference signal and a sample signal.

5. The invention in accordance with claim 1 further comprising a temperature control device for controlling the temperature of said photodiode array to compensate for changes in temperature of the analyzer.

6. The invention in accordance with claim 5 wherein said temperature control device is a heater.

7. The invention in accordance with claim 1 further comprising collimating optics between said light source and said sample chamber for collimating said beam of light.

8. The invention in accordance with claim 1 further comprising a focusing lens between said sample chamber and said entrance slit of said spectrometer for focusing said beam of light on said slit.

9. The invention in accordance with claim 1 wherein said near infrared spectrum is between about 700 and 2500 nm.

10. The invention in accordance with claim 1 wherein said infrared spectrum is between about 800 and 1000 nm.

11. The invention in accordance with claim 1 wherein said bands of near infrared wavelengths of said individual photodiodes is between about 5 and 10 nm.

12. The invention in accordance with claim 1 wherein said wherein said electronic circuitry can automatically process a reference and a sample signal.

13. The invention in accordance with claim 12 further comprising an off-axis photo detector to distinguish between said reference and sample signal, wherein said photodiode signals are processed in parallel, wherein said count is inversely proportional to the intensity of incident light on said photodiodes, and wherein said reference voltage and said timer circuits are variable having high level settings for said reference signal and low level settings for said sample signal.

14. The invention in accordance with claim 13 wherein the dimensions of said slit are substantially the same as the dimensions of said individual photodiodes.

* * * * *